United States Patent [19]
Kranzler et al.

[11] Patent Number: 5,614,284
[45] Date of Patent: Mar. 25, 1997

[54] LAMINATED PATCH TISSUE REPAIR SHEET MATERIAL

[75] Inventors: Thane L. Kranzler; Michael L. McDonald, both of Flagstaff, Ariz.

[73] Assignee: W. L. Gore & Associates, Inc., Newark, Del.

[21] Appl. No.: 423,908

[22] Filed: Apr. 13, 1995

Related U.S. Application Data

[62] Division of Ser. No. 19,394, Feb. 18, 1993, Pat. No. 5,433,996.

[51] Int. Cl.⁶ ........................................ B32B 3/10
[52] U.S. Cl. ................ 428/138; 428/315.5; 428/315.7; 428/317.1; 428/317.7; 428/318.6; 428/319.7; 623/11
[58] Field of Search ................ 428/138, 315.5, 428/315.7, 317.1, 317.7, 318.6, 319.7; 623/11

[56] References Cited

U.S. PATENT DOCUMENTS

| | | |
|---|---|---|
| 3,124,136 | 3/1964 | Usher . |
| 3,944,477 | 3/1976 | Argade ................................ 204/266 |
| 3,953,566 | 4/1976 | Gore . |
| 4,187,390 | 2/1980 | Gore . |
| 4,313,805 | 2/1982 | Burney et al. . |
| 4,385,093 | 5/1983 | Hubis . |
| 4,478,665 | 10/1984 | Hubis . |
| 4,482,516 | 11/1984 | Bowman et al. . |
| 4,598,011 | 7/1986 | Bowman . |
| 4,983,434 | 1/1991 | Sassa . |
| 5,032,445 | 7/1991 | Scantlebury . |

FOREIGN PATENT DOCUMENTS

| | | |
|---|---|---|
| 9210218 | 6/1992 | WIPO . |
| 9317635 | 9/1993 | WIPO . |

*Primary Examiner*—Christopher Raimund
*Attorney, Agent, or Firm*—Wayne D. House

[57] ABSTRACT

A sheet of implantable patch tissue repair material having the form of a layer of porous polytetrafluoroethylene sheet material laminated to a layer of mesh-type sheet material having a multiplicity of openings through the mesh-type sheet material, said openings having a mean minimum diameter of about 0.1 mm. The inventive patch tissue repair material offers good strength characteristics, good biocompatibility, suture retention, and flexibility.

19 Claims, 1 Drawing Sheet

LAMINATED PATCH TISSUE REPAIR SHEET MATERIAL

This application is a division of application Ser. No. 08/019,394, filed Feb. 18, 1993 now U.S. Pat. No. 5,433, 996.

FIELD OF THE INVENTION

This invention relates to the field of implantable sheet materials useful for the repair of living tissue and particularly for hernia repairs.

BACKGROUND OF THE INVENTION

Implantable sheet materials for tissue repair are well known. Tissue defects commonly repaired with these materials include wounds of the abdominal wall and in particular hernia repairs. Wounds of the chest wall, diaphragm and other weaknesses of the musculoaponeurotic tissues are also repaired with these materials.

There are two fundamental types of sheet materials that are most predominantly used. The first type is a mesh material having a multiplicity of openings through the material, such as Marlex® Mesh available from C. R. Bard, Inc., Billerica, Mass. This is an open mesh knitted from polypropylene monofilament of about 0.17 mm diameter and having openings of about 0.54 mm diameter. These mesh materials offer good suture retention, good mechanical strength, and allow tissue to grow through the mesh openings.

An alternative type of implantable sheet material for tissue repair is GORE-TEX® Soft Tissue Patch made from porous expanded polytetrafluoroethylene, available from W. L. Gore & Associates, Inc., Flagstaff, Ariz. in 1.0 and 2.0 mm thicknesses. This is a porous sheet material that does not contain large, macroporous holes in the fashion of a mesh. Because there are no large holes for tissue to grow through and around, this material is useful when it is desirable to minimize the risk of tissue adhesion.

SUMMARY OF THE INVENTION

The present invention is a sheet of implantable patch tissue repair material comprising a layer of porous polytetrafluoroethylene sheet material laminated to a layer of mesh-type sheet material having a multiplicity of macroporous openings through the mesh-type sheet material, said openings having a mean minimum diameter of about 0.1 mm. The inventive patch tissue repair material offers good strength characteristics, good biocompatibility, suture retention, and flexibility.

The term laminated is used herein to describe the bonding together of two layers of material in any fashion that prevents subsequent separation of the layers during ordinary use. Macroporous openings are herein considered to be openings visible to the human eye without magnification, and visibly open through the thickness of the layer through which the openings have been formed. Microporous openings require the use of magnification to make them visible to the human eye.

DETAILED DESCRIPTION OF THE INVENTION

Figure 1:
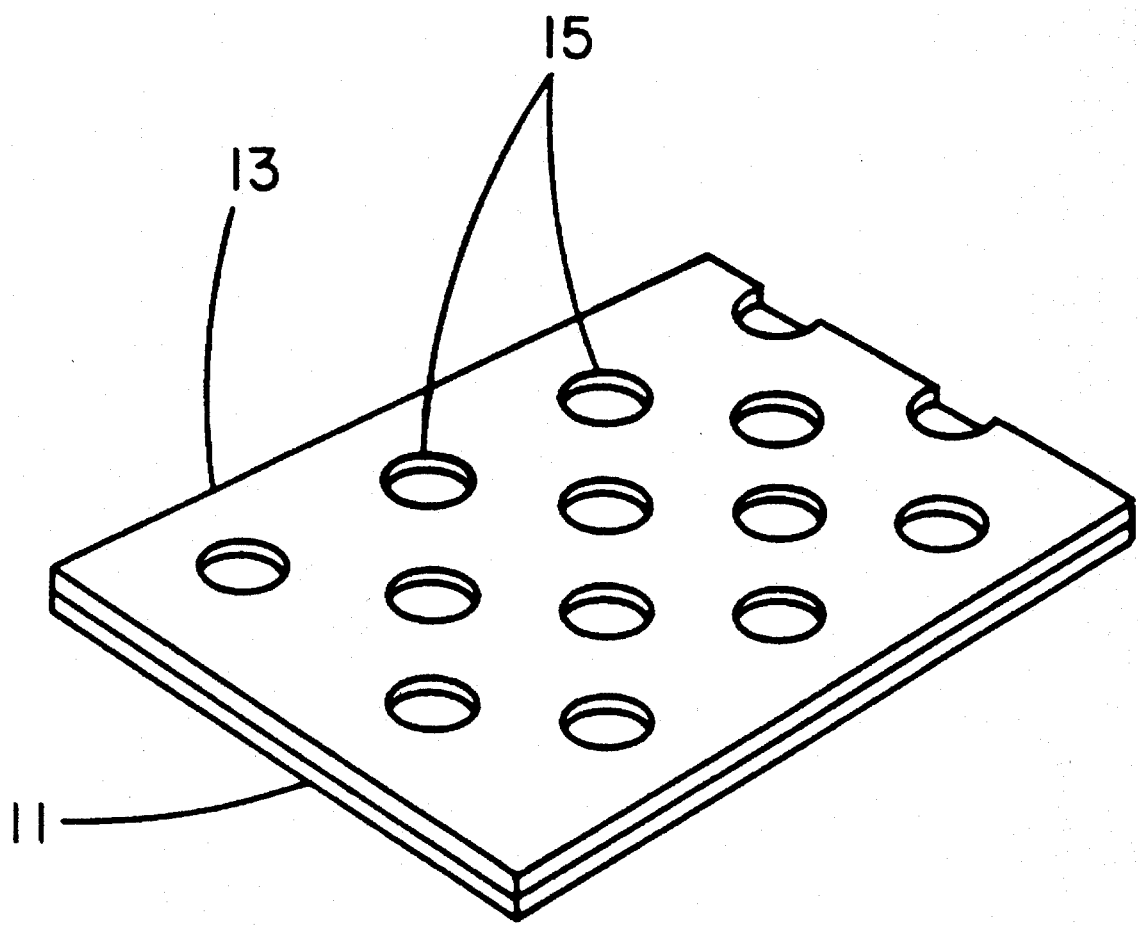
FIG. 1 describes a perspective view of the laminated patch tissue repair sheet material of the present invention.
Figure 2:
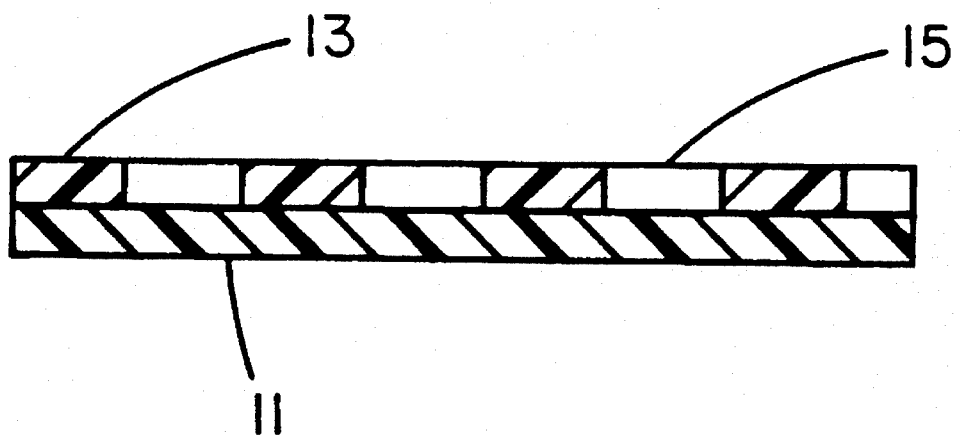
FIG. 2 describes a cross section of the laminated patch tissue repair sheet material of the present invention.

FIG. 1 shows a perspective view of the laminated patch tissue repair sheet material of the present invention having a layer 11 of porous PTFE laminated to a layer 13 of mesh-type sheet material having a multiplicity of openings through the mesh-type sheet material. FIG. 2 describes a cross section of the laminated patch tissue repair sheet material.

The openings through the mesh-type sheet material should be of at least about 0.1 mm diameter. The general shape of the opening is not believed to be of any biological importance and can therefore be round, elliptical, triangular, square, rectangular, hexagonal, etc. For non-circular openings having a length or long diameter and a width or short diameter, the term minimum diameter is defined herein as the maximum dimension, measured substantially parallel to the surface of the sheet material, that describes the width or short diameter of the non-circular opening. The minimum diameter is to be measured with the sample in a relaxed state with no deforming force. The mean minimum diameter is determined by randomly selecting a sample area containing at least 10 macroscopic openings, locating and measuring the minimum diameter of the ten largest openings within that area and calculating the mean diameter of those ten openings. If it is not possible to obtain a sample containing at least ten openings, then all openings within the area of the largest sample obtainable should be included in the calculation of the mean value.

The layer 13 of the mesh-type sheet material may be any suitable biocompatible material including polypropylene, polyethylene terephthalate, PTFE or microporous PTFE. The mesh-type sheet material may be in the form of a sheet from which the openings 15 have been cut or otherwise formed, or alternatively may be an open fabric such as a knit or a weave having a multiplicity of openings formed by widely spaced strands of the fabric.

The layer 11 of microporous PTFE is preferably microporous expanded PTFE made according to the teachings of U.S. Pat. Nos. 3,953,566 and 4,187,390. This material has a microstructure of nodes interconnected by fibrils. It may also be made according to U.S. Pat. Nos. 4,482,516 and 4,598,011 if a high strength material with a coarse microstructure is desired. Layer 11 may optionally be made as a laminate of multiple layers as taught by U.S. Pat. Nos. 4,385,093 and 4,478,665.

Layers 11 and 13 may be laminated by at least two different methods. First, adhesives may be used to adhere the two layers. One such suitable adhesive is Silastic® Medical Adhesive Silicone Type A (Catalog no. 891) from Dow Corning, Midland, Mich. A thermoplastic adhesive such as Teflon FEP 120 Aqueous Dispersion from E. I. DuPont de Nemours, Wilmington, Del. may be used. A coating of the FEP dispersion is applied to the side of the mesh-type layer 13 which is intended to be adhered to the porous PTFE layer 11. The two layers are then adhered by the application of heat and pressure (as for example applied by opposing rollers) with enough heat applied to cause melting of the Teflon FEP 120 Dispersion, about 290° C.

Alternatively, layers 11 and 13 may be laminated by the use of heat and pressure without the use of an additional adhesive. This has been found to be the preferred method when the mesh-type layer 13 of a material having a lower melting point than that of the porous PTFE layer 11. For example, when a layer 13 of mesh-type polypropylene is used, it was found that heating the polypropylene layer to about 180° C., which is in excess of the melting point of polypropylene, while simultaneously applying pressure in a direction perpendicular to the planes of layers 11 and 13 resulted in good adhesion between the two layers.

It was also found possible to form both layers 11 and 13 from porous expanded PTFE sheet materials. A sheet of 1 mm thick GORE-TEX Soft Tissue Patch material of about 6 cm×6 cm, was used for the mesh layer 13 by forming holes 15 through the layer 13 by using a round punch of about 3 mm diameter. The holes were spaced about 1.2 cm apart. Layer 13 was then laminated with the use of heat and pressure to a second layer 11 of GORE-TEX Soft Tissue Patch material wherein layer 11 contained no holes. Lamination was accomplished by placing layers 11 and 13 between two plates heated to 380° C. and applying about 1.3 kg/cm$^2$ pressure to the two layers. The heated plates were allowed to cool to about 300° C. while the pressure was maintained. At the end of this time the pressure was released and the two laminated layers 11 and 13 of porous expanded PTFE were removed. Laminated layers 11 and 13 were found to be well adhered in that repeated flexing of the laminated layers showed no inclination of the layers to separate.

We claim:

1. A sheet of implantable patch tissue repair material comprising a first layer of porous polytetrafluoroethylene sheet material laminated to a second layer of sheet material, said sheet of implantable patch tissue repair material having a maximum thickness and having a multiplicity of macroscopic openings in the second layer extending into at least half of the maximum thickness of the sheet of implantable patch tissue repair material wherein the mean minimum diameter of the openings is at least about 0.1 mm.

2. A sheet of implantable patch tissue repair material according to claim 1 wherein the second layer of sheet material is comprised of an implantable material selected from the group consisting of polypropylene, polyethylene terephthalate and polytetrafluoroethylene.

3. A sheet of implantable patch tissue repair material according to claim 2 wherein the second layer is comprised of porous polytetrafluoroethylene.

4. A sheet of implantable patch tissue repair material according to claim 3 wherein the first layer of porous polytetrafluoroethylene is laminated to the second layer of sheet material by thermal bonding.

5. A sheet of implantable patch tissue repair material according to claim 3 wherein the second layer of porous polytetrafluoroethylene has a microstructure of nodes interconnected by fibrils.

6. A sheet of implantable patch tissue repair material according to claim 5 wherein the first layer of porous polytetrafluoroethylene is laminated to the second layer of sheet material by thermal bonding.

7. A sheet of implantable patch tissue repair material according to claim 1 wherein the first layer of porous polytetrafluoroethylene has a microstructure of nodes interconnected by fibrils.

8. A sheet of implantable patch tissue repair material according to claim 7 wherein the second layer of sheet material is comprised of an implantable material selected from the group consisting of polypropylene, polyethylene terephthalate and polytetrafluoroethylene.

9. A sheet of implantable patch tissue repair material according to claim 8 wherein the first layer of porous polytetrafluoroethylene is laminated to the second layer of sheet material by thermal bonding.

10. A sheet of implantable patch tissue repair material according to claim 6 wherein the second layer of sheet material is comprised of porous polytetrafluoroethylene.

11. A sheet of implantable patch tissue repair material according to claim 10 wherein the first layer of porous polytetrafluoroethylene is laminated to the second layer of sheet material by thermal bonding.

12. A sheet of implantable patch tissue repair material according to claim 10 wherein the second layer of porous polytetrafluoroethylene has a microstructure of nodes interconnected by fibrils.

13. A sheet of implantable patch tissue repair material according to claim 12 wherein the first layer of porous polytetrafluoroethylene is laminated to the second layer of sheet material by thermal bonding.

14. A sheet of implantable patch tissue repair material according to claim 1 wherein the first layer of porous polytetrafluoroethylene sheet material is laminated to the second layer of sheet material by an adhesive.

15. A sheet of implantable patch tissue repair material according to claim 14 wherein the adhesive is silicone adhesive.

16. A sheet of implantable patch tissue repair material according to claim 14 wherein the adhesive is a fluoropolymer adhesive.

17. A sheet of implantable patch tissue repair material according to claim 14 wherein the adhesive is a fluorinated ethylene propylene adhesive.

18. A sheet of implantable patch tissue repair material according to claim 14 wherein the adhesive is a thermoplastic adhesive.

19. A sheet of implantable patch tissue repair material according to claim 1 wherein the first layer of porous polytetrafluoroethylene sheet material is laminated to the second layer of sheet material by thermal bonding.

* * * * *